United States Patent
Kim et al.

(10) Patent No.: US 10,557,813 B2
(45) Date of Patent: Feb. 11, 2020

(54) OCCUPANT CLASSIFICATION APPARATUS

(71) Applicant: Hyundai Motor Company, Seoul (KR)

(72) Inventors: Nam Gyun Kim, Yeonsu-gu (KR); Chun Seok Park, Bucheon-si (KR)

(73) Assignee: Hyundai Motor Company, Seoul (KR)

( * ) Notice: Subject to any disclaimer, the term of this patent is extended or adjusted under 35 U.S.C. 154(b) by 286 days.

(21) Appl. No.: 15/374,226

(22) Filed: Dec. 9, 2016

(65) Prior Publication Data

US 2018/0031511 A1  Feb. 1, 2018

(30) Foreign Application Priority Data

Jul. 26, 2016 (KR) .................. 10-2016-0095009

(51) Int. Cl.
*G01N 27/22* (2006.01)
*G01N 27/12* (2006.01)
*G01N 27/04* (2006.01)

(52) U.S. Cl.
CPC ......... *G01N 27/228* (2013.01); *G01N 27/048* (2013.01); *G01N 27/127* (2013.01); *G01N 27/227* (2013.01)

(58) Field of Classification Search
CPC ... G01N 27/227; G01N 27/127; G01N 27/048
See application file for complete search history.

(56) References Cited

U.S. PATENT DOCUMENTS

| | | | |
|---|---|---|---|
| 6,161,070 A | 12/2000 | Jinno et al. | |
| 7,032,448 B2* | 4/2006 | Hamamoto | G01N 27/225 361/280 |
| 8,237,455 B2 | 8/2012 | Griffin | |
| 2006/0187038 A1 | 8/2006 | Shieh et al. | |
| 2008/0180234 A1* | 7/2008 | Yamanaka | B60N 2/002 340/438 |
| 2009/0033078 A1* | 2/2009 | Hawes | B60N 2/002 280/735 |
| 2011/0006788 A1* | 1/2011 | Kim | B60N 2/002 324/661 |
| 2011/0221453 A1* | 9/2011 | Hwang | G01G 7/00 324/661 |
| 2011/0221459 A1* | 9/2011 | Uno | B60N 2/002 324/713 |

(Continued)

FOREIGN PATENT DOCUMENTS

| | | |
|---|---|---|
| EP | 2353946 A1 | 8/2011 |
| JP | 2008-027807 A | 2/2008 |

(Continued)

*Primary Examiner* — Alvaro E Fortich
(74) *Attorney, Agent, or Firm* — Morgan, Lewis & Bockius LLP

(57) ABSTRACT

An occupant classification apparatus configured for classifying an occupant seated in a seat based on capacitance of and the amount of moisture contained in the occupant is disclosed. The occupant classification apparatus includes an electrode device for detecting an occupant seated in a seat, an occupant property measurement device for measuring capacitance of and the amount of moisture contained in the occupant detected by the electrode device, and a controller configured for estimating the occupant based on the capacitance and the amount of moisture measured by the occupant property measurement device.

11 Claims, 8 Drawing Sheets

(56) References Cited

U.S. PATENT DOCUMENTS

| | | | | |
|---|---|---|---|---|
| 2012/0161777 A1* | 6/2012 | Nakagawa | ............. | B60N 2/002 |
| | | | | 324/457 |
| 2012/0161793 A1* | 6/2012 | Satake | ................... | B60N 2/002 |
| | | | | 324/658 |
| 2014/0291523 A1* | 10/2014 | Kwon | .................... | B60N 2/002 |
| | | | | 250/341.7 |

FOREIGN PATENT DOCUMENTS

| JP | 2011-095267 A | 5/2011 |
|---|---|---|
| JP | 2013-186036 A | 9/2013 |
| KR | 10-2006-0051042 A | 5/2006 |
| KR | 10-2008-0098375 A | 11/2008 |
| KR | 10-2009-0052713 A | 5/2009 |

\* cited by examiner

OCCUPANT CLASSIFICATION APPARATUS

CROSS-REFERENCE TO RELATED APPLICATION

The present application claims priority to Korean Patent Application No. 10-2016-0095009, filed on Jul. 26, 2016, the entire contents of which is incorporated herein for all purposes by this reference.

BACKGROUND OF THE INVENTION

Field of the Invention

The present invention relates to an occupant classification apparatus and, more particularly, to an occupant classification apparatus configured for classifying an occupant seated in a seat based on capacitance of and the amount of moisture contained in the occupant.

Description of Related Art

Generally, an occupant classification system (OCS) classifies an occupant (a passenger or an object) seated in a seat.

Such an occupant classification system is implemented in various manners. For example, one conventional occupant classification apparatus includes an individual sensor mat mounted per seat. This sensor mat measures a pressure distribution, estimates the type of an occupant, and delivers information to a vehicle control system, thereby performing vehicle control suitable for the estimated occupant. Control using the information on the occupant estimated by the occupant classification apparatus includes airbag control or belt retractor control.

However, a conventional occupant classification apparatus based on a pressure distribution alone cannot accurately estimate the type of the occupant. In addition, another conventional occupant classification apparatus for estimating an occupant based on impedance of the occupant can relatively accurately estimate the occupant but may increase the number of parts due to use of an AC voltage and should use expensive parts, thereby increasing costs.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing an occupant classification apparatus capable of easily classifying an occupant seated in a seat based on capacitance of and the amount of moisture contained in the occupant.

In accordance with one aspect of the present invention, the above and other objects can be accomplished by the provision of an occupant classification apparatus including an electrode device for detecting an occupant seated in a seat, an occupant property measurement device for measuring capacitance of and the amount of moisture contained in the occupant detected by the electrode device, and a controller for estimating the occupant based on the capacitance and the amount of moisture measured by the occupant property measurement device.

In the exemplary embodiment of the present invention, the electrode device may include first and second electrodes mounted to overlap each other and configured to receive a voltage and to generate an electric field.

In the exemplary embodiment of the present invention, the first electrode may be placed adjacent to an area, in which the occupant is seated, of the seat, the second electrode may be placed at an opposite side thereof, and a first-electrode-direction electric field generated by the second electrode may block a second-electrode-direction electric field generated by the first electrode.

In the exemplary embodiment of the present invention, the occupant property measurement device includes a discharge response signal generator for generating a discharge response signal corresponding to an amount of charge stored according to capacitance of the occupant detected by the electrode device, a capacitance determination device for generating a signal capable of estimating the capacitance of the occupant from the discharge response signal, and a moisture detector for detecting the amount of moisture according to change in electrical resistance of the occupant detected by the electrode device.

In the exemplary embodiment of the present invention, the discharge response signal generator may apply a direct current (DC) power supply voltage to the electrode device to store charge according to the capacitance of the occupant detected by the electrode device and discharge the charge stored according to the capacitance of the occupant to generate the discharge response signal corresponding to the amount of charge stored according to the capacitance of the occupant.

In the exemplary embodiment of the present invention, the discharge response signal generator may include a power supply for providing the power supply voltage to the electrode device; a detection capacitor; and a switch for selectively determining an electrical connection between the electrode device and the power supply and an electrical connection between the electrode device and the detection capacitor. When the switch establishes the electrical connection between the electrode device and the detection capacitor, a power supply voltage is applied to the detection capacitor during a predetermined time period, and a voltage of the detection capacitor is the discharge response signal.

In the exemplary embodiment of the present invention, the controller controls the switch to establish the electrical connection between the electrode device and the detection capacitor in a state of establishing the electrical connection between the electrode device and the power supply to perform charging by the capacitance of the occupant detected by the electrode device, such that the charge stored according to the capacitance of the occupant detected by the electrode device is discharged, the discharged charge is provided to the detection capacitor to form an initial voltage of the detection capacitor, and the detection capacitor is charged by the power supply voltage provided during the predetermined time period after forming the initial voltage.

In the exemplary embodiment of the present invention, the capacitance determination device may output a signal including change in the voltage of the detection capacitor increasing from the initial voltage as a signal capable of estimating the capacitance.

In the exemplary embodiment of the present invention, the capacitor determination device may include a reference signal generator for generating a reference signal having a logic high value in a period in which the voltage of the detection capacitor increases from the initial voltage and having a logic low value before the voltage of the detection capacitor decreases to a predetermined reference voltage or less after increasing the voltage of the detection capacitor, and a NAND logic element for receiving the voltage of the detection capacitor and the reference signal and outputting a result of performing a NAND logic operation with respect to the received signals.

In the exemplary embodiment of the present invention, the moisture detector may detect change in current according to change in electrical resistance of the occupant detected by the electrode device in a state of applying a DC voltage to the electrode device to detect the amount of moisture contained in the occupant.

In the exemplary embodiment of the present invention, the controller may include ranges associated with the capacitance of and the amount of moisture contained in the occupant according to occupant type and determine a critical range, to which the capacitance and the amount of moisture measured by the occupant property measurement device belong, to determine the type of the occupant seated in the seat.

As another aspect of the present invention, an occupant classification apparatus includes an electrode device for receiving a direct current (DC) power supply voltage such that an electric field is formed in a measurement area, in which an occupant is located, to sense the occupant seated in a seat, an occupant property measurement device for providing the DC power supply voltage to the electrode device, generating a signal corresponding to capacitance of the occupant based on a signal generated by discharging charge stored according to the capacitance of the occupant detected in the measurement area and generating a signal corresponding to the amount of moisture contained in the occupant based on change in electrical resistance of the occupant detected in the measurement area, and a controller for estimating the occupant based on a signal corresponding to the capacitance of the occupant and a signal corresponding to the amount of moisture contained in the occupant.

In the exemplary embodiment of the present invention, the occupant property measurement device may selectively and electrically connect the electrode device to the DC power supply voltage and a detection capacitor under control of the controller, and perform charging by the capacitance of the occupant detected in the measurement area, when an electrical connection between the electrode device and the DC power supply voltage is established, and discharge charge stored according to the capacitance of the occupant detected in the measurement area, provide the discharged charge to the detection capacitor to form an initial voltage of the detection capacitor and charge the detection capacitor by the power supply voltage during a predetermined time period after forming the initial voltage, when an electrical connection between the electrode device and the detection capacitor is established.

In the exemplary embodiment of the present invention, the occupant property measurement device may output information based on a time required for the voltage of the detection capacitor to increase from the initial voltage to a predetermined reference voltage as a signal corresponding to the capacitance of the occupant.

Since the occupant classification apparatuses according to an exemplary embodiment of the present invention can detect change in voltage generated by discharging charge stored according to capacitance of an occupant and change in current according to the amount of moisture contained in the occupant to estimate the occupant, an algorithm requiring complex operation is not required to classify occupants and the occupant can be easily classified.

since the occupant classification apparatus can estimate the occupant by applying a low DC voltage, it is possible to omit several parts used for applying an AC voltage in a conventional occupant classification apparatus and, more expensive parts. Therefore, it is possible to reduce costs.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
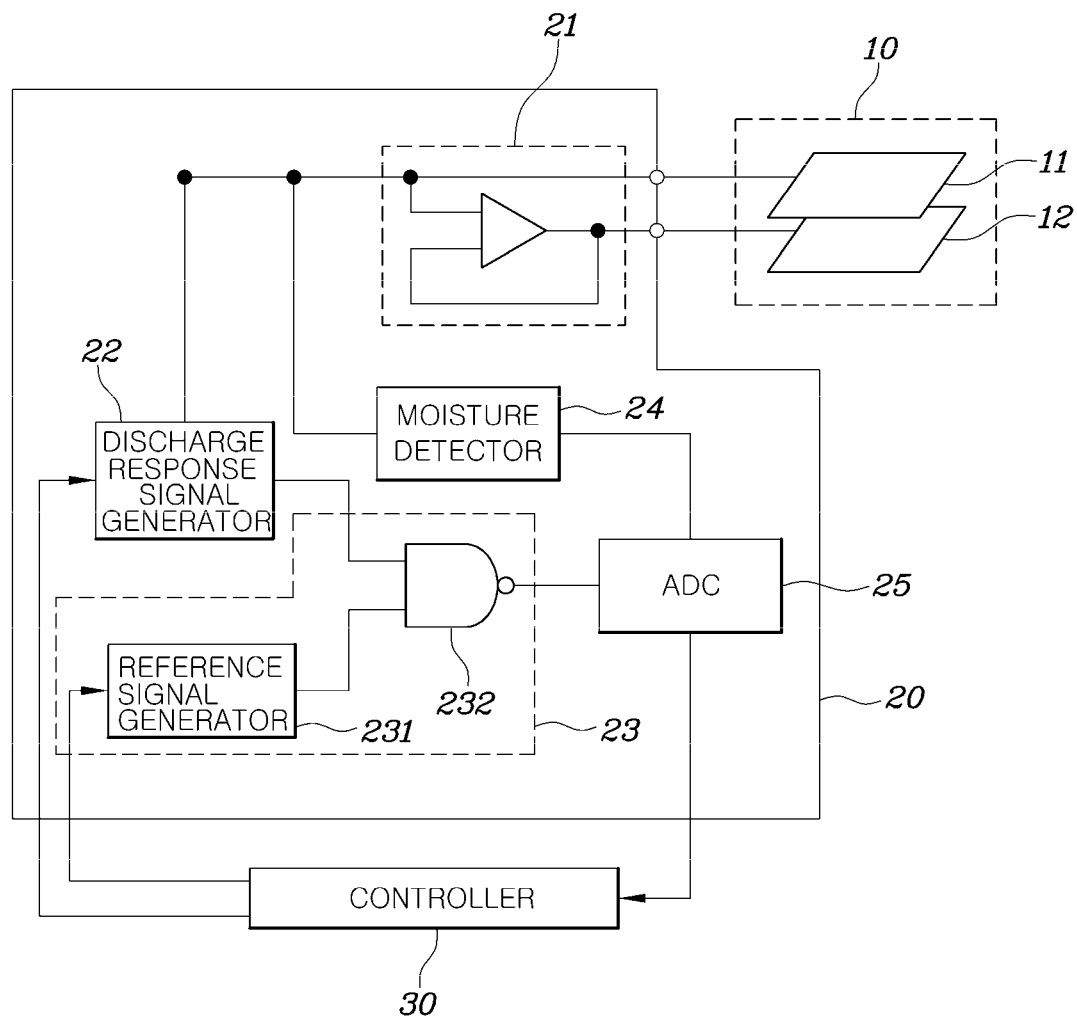
FIG. 1 is a block diagram showing an occupant classification apparatus an exemplary embodiment according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, occupant classification apparatuses according to various embodiments of the present invention will be described in detail with reference to the accompanying drawings.

FIG. 1 is a block diagram showing an occupant classification apparatus an exemplary embodiment according to an exemplary embodiment of the present invention.

Referring to FIG. 1, the occupant classification apparatus according to the exemplary embodiment of the present invention includes an electrode device 10, an occupant property measurement device 20 and a controller 30.

The electrode device 10 is mounted at a specific position of each seat to sense an occupant sitting in a seat or an object placed in a seat.

In one exemplary embodiment of the present invention, the electrode device 10 may include a first electrode 11 and a second electrode overlapping each other. Each of the first electrode 11 and the second electrode 12 generates an electric field by an applied voltage and receives a DC voltage to form an electric field in one exemplary embodiment of the present invention.

The first electrode 11 and the second electrode 12 may include the same material in the same shape or may include different materials in different shapes in consideration of the positions thereof or electrical characteristics to be sensed. Each of the first electrode 11 and the second electrode 12 may include a material having electrical conductivity including steel or foil, and may have a plate shape to form an electric field in a relatively large range.

Figure 2:
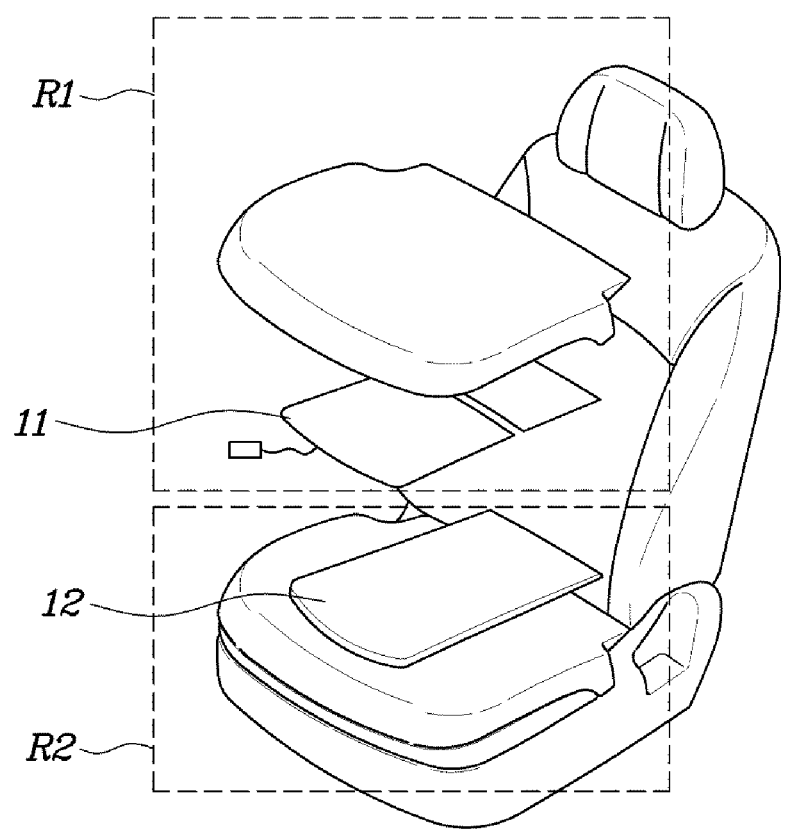
FIG. 2 is a diagram showing an example of installing an electrode device applied to an occupant classification apparatus an exemplary embodiment according to an exemplary embodiment of the present invention.

FIG. 2 is a diagram showing an example of installing an electrode device applied to an occupant classification apparatus an exemplary embodiment according to an exemplary embodiment of the present invention.

As shown in FIG. 2, the electronic device 10 may be mounted in a seat cushion of a seat. The first electrode 11 is placed adjacent to an area of a seat in which an occupant is seated and the second electrode 12 may be placed at the opposite side thereof. By mounting the electrode device 10, a measurement area R1 may be formed above the first electrode 11 and a guard area R2 may be formed below the second electrode 12. The measurement area R1 may be an area in which a first-direction electric field of the first electrode 11 is formed to measure capacitance and resistance of the occupant seated in the upper surface of the seat cushion. In addition, the guard area R2 is an area in which an electric field of the second electrode 12 is generated. The first-direction electric field of the second electrode 12 may block a second-direction electric field of the first electrode 11, such that the directivity of the electric field of the first electrode 11 is set to the first direction. In the example shown in FIG. 2, the first direction is an upper direction corresponding to the position of the occupant with respect to the first electrode 11 and the second electrode 12 and the second direction is a lower direction which is at an angle of 180 degrees from the first direction.

In one exemplary embodiment of the present invention, the potentials of the first electrode 11 and the second electrode 12 may be equal such that the first-direction electric field of the second electrode 12 blocks the second-direction electric field of the first electrode 11. In another exemplary embodiment of the present invention, the first electrode 11 and the second electrode 12 may have a constant small potential difference to decrease influence of the second-direction electric field of the first electrode 11 on a measured value.

In several embodiments of the present invention, when an occupant is located in the measurement area R1 of the seat, unique capacitance and electrical resistance of the occupant are delivered to the electrode device 10 by the electric field formed in the measurement area R1. In other words, when an occupant is located in the measurement area in a state in which a specific voltage is applied to the electrode device 10 such that an electric field is formed in the measurement area by the electrode device 10, the unique capacitance and electrical resistance of the occupant are applied between the electrode device 10 and the ground. In several embodiments of the present invention, an occupant is estimated by detecting the amount of moisture according to the unique capacitance and electrical resistance of the occupant.

In FIG. 1, a voltage follower circuit 21 using an operational amplifier is provided in the occupant property measurement device 20. The voltage follower circuit 21 may be used to equalize the potentials of the first electrode 11 and the second electrode 12. Although not shown, by adding a resistor to the output terminal of the voltage follower circuit 21, the first electrode 11 and the second electrode 12 may have a constant small potential difference.

Although the voltage follower circuit 21 is shown as being provided in the occupant property measurement device 20 in FIG. 1, the voltage follower circuit 21 may be provided outside the occupant property measurement device 20.

Figure 3:
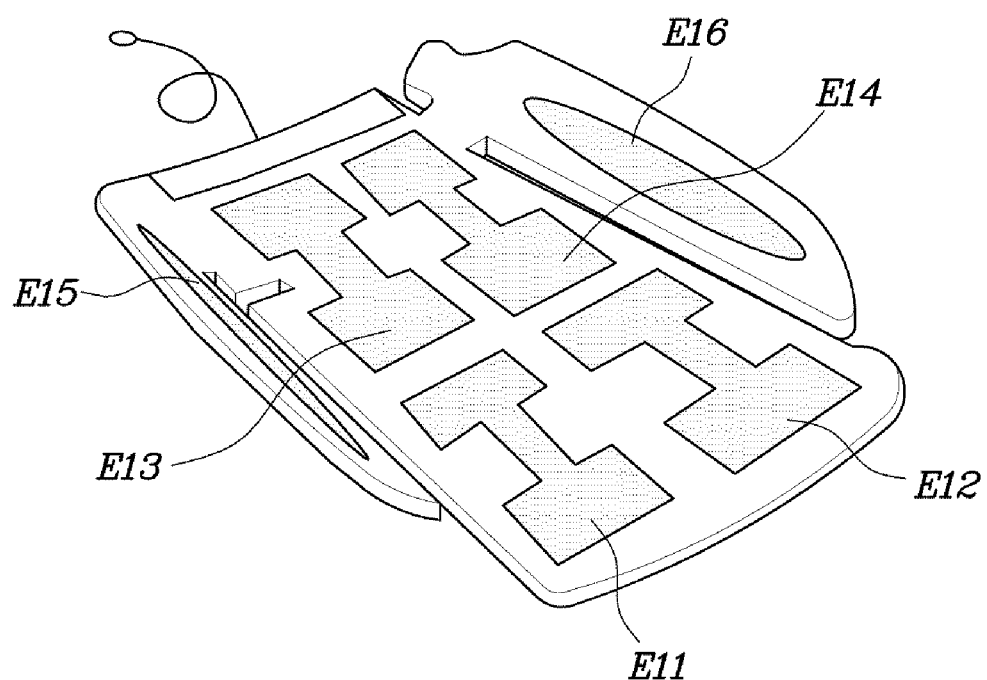
FIG. 3 and FIG. 4 are diagrams illustrating a multi-electrode structure in which an electrode device applied to an occupant classification apparatus an exemplary embodiment according to an exemplary embodiment of the present invention is implemented by a plurality of separated electrodes.
Figure 4:
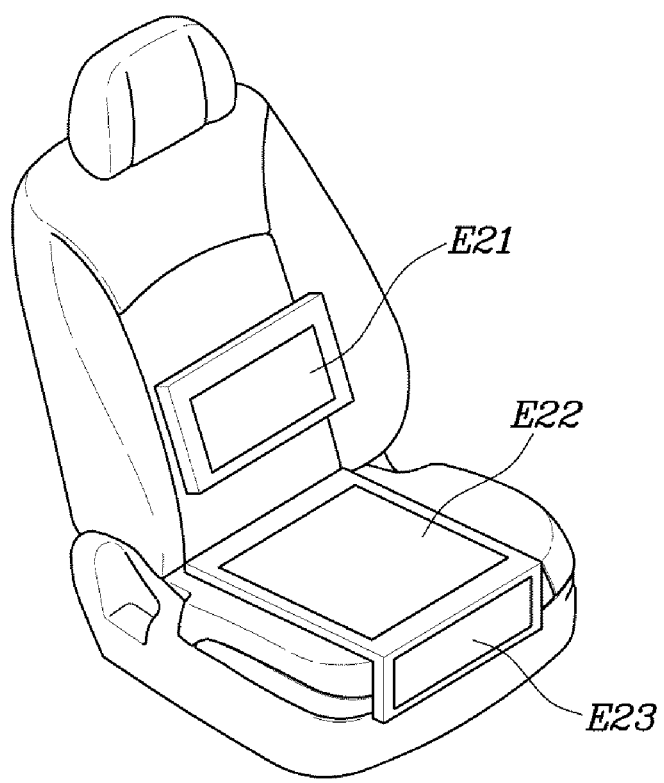

FIG. 3 and FIG. 4 are diagrams illustrating a multi-electrode structure in which an electrode device applied to an occupant classification apparatus an exemplary embodiment according to an exemplary embodiment of the present invention is implemented by a plurality of separate electrodes.

In one exemplary embodiment of the present invention, the electrode device 10 may include multiple electrodes E11 to E16 as shown in FIG. 3 and FIG. 4, to sense various postures of an occupant or a small occupant placed in a portion of the seat. In the instant case, the occupant classification apparatus according to one exemplary embodiment of the present invention may sense the type and posture of the occupant using the capacitance and electrical resistance detected using the multiple electrodes E11 to E16 placed at specific positions.

For example, the electrode device 10 may include multiple electrodes E21 to E23 placed at a back of a seat and a seat cushion as shown in FIG. 4 to sense the size of the occupant seated in the seat. In the example of FIG. 4, the electrode E21 may serve to sense the body of the occupant and the electrodes E22 and E23 may serve to sense the hips and calves of the occupant.

Referring to FIG. 1 again, the occupant property measurement device 20 measures the capacitance of and amount of moisture contained in the occupant seated in the seat through the electrode device 10. As shown in FIG. 1, the occupant property measurement device 20 may include a discharge response signal generator 22, a capacitance determination device 23, a moisture detector 24 and an analog/digital converter 25.

The discharge response signal generator 22 may apply a DC voltage having a constant level to the electrode device 10 to store charge according to the capacitance of the occupant detected by the electrode device 10 and then discharge the charge stored according to the capacitance of the occupant detected by the electrode device 10 to generate a discharge response signal corresponding to the amount of charge stored according to the capacitance of the occupant detected by the electrode device 10.

Figure 5:
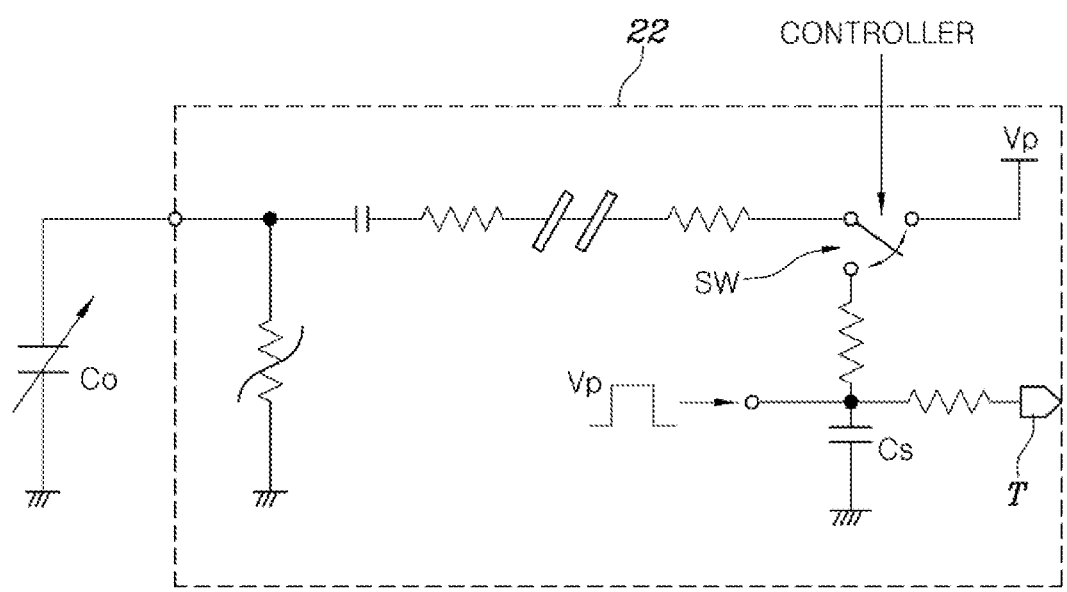
FIG. 5 is a circuit diagram showing a discharge response signal generator included in an occupant classification apparatus an exemplary embodiment according to an exemplary embodiment of the present invention in detail.

The detailed configuration of the discharge response signal generator 22 is shown in FIG. 5.

FIG. 5 is a circuit diagram showing a discharge response signal generator included in an occupant classification apparatus an exemplary embodiment according to an exemplary embodiment of the present invention.

Referring to FIG. 5, the discharge response signal generator 22 may include a power supply for outputting a power supply voltage Vp and a switch SW for selectively and electrically connecting a connection line between the power supply and the electrode device 10 and a detection capacitor Cs. In FIG. 5, reference numeral "Co" indicates capacitance of the occupant detected by the electrode device 10. Accordingly, the electrode device 10 may be understood as being connected to a node connected to the capacitor indicating the capacitance of the occupant. The resistors, capacitors and electrical elements, which are not denoted by reference numerals in FIG. 5, may be omitted or added according to circuit configuration and may not be directly related to the technical scope of the present invention.

The power supply supplies the power supply voltage Vp. The power supply voltage Vp supplied by the power supply may maintain electrical connection to the electrode device 10 to store charge by the unique capacitance Co of the occupant.

The contact point of the switch SW may be determined by a control signal provided by the controller 30. In an initial state, the switch SW may be switched to supply the power supply voltage Vp to the capacitor Co of the occupant, charging the capacitor Co of the occupant.

Subsequently, the switch SW operates to electrically connect the detection capacitor Cs to the electrode device 10 during a very short time, under control of the controller 30. When the detection capacitor Cs is connected to the electrode device 10 by the switch SW, charge stored by the unique capacitance Co of the occupant and the capacitance of the circuit are discharged and the detection capacitor Cs is charged to generate a voltage. The switch SW is switched to supply the power supply voltage Vp to the electrode device 10 after establishing an electrical connection between the electrode device 10 and the detection capacitor Cs during the very short time. While the switch SW is switched to electrically connect the detection capacitor Cs to the electrode device 110 by the controller 30, the power supply voltage is supplied to the detection capacitor Cs during a predetermined time period. That is, the detection capacitor Cs is initially charged during a short time by receiving the charge stored according to the capacitance of the circuit by switching of the switch SW, and then is continuously charged by the power supply voltage Vp supplied during a predetermined time period.

For example, when the switch SW is switched to supply the power supply voltage Vp of the power supply to the electrode device 10, charging is performed according to the capacitance Cc of the circuit configuring the discharge response signal generator 22 and the capacitance Co of the occupant according to supply of the power supply voltage Vp. This may be expressed by Equation 1 below.

$$Q1 = Vp \times (Co + Cc) \qquad \text{Equation 1}$$

where, the capacitance of the circuit may be regarded as a sum of the capacitance of the capacitor included in the circuit and the capacitance of a parasitic component. That is, in a state in which the detection capacitor Cs is not electrically connected to the line for connecting the power supply and the electrode device 10, the capacitor corresponding to the capacitance Co of the occupant and the capacitor corresponding to the capacitance Cc of the circuit are connected to the power supply voltage Vp in parallel, performing charging.

Subsequently, when the switch SW is switched to electrically connect the electrode device 10 and the detection capacitor Cs under control of the controller 30, charge stored according to the capacitance Cc of the circuit configuring the discharge response signal generator 22 and the capacitance Co of the occupant move to the detection capacitor Cs to charge the detection capacitor Cs, forming an initial voltage of the detection capacitor Cs. That is, the capacitance Cs of the detection capacitor is added to the circuit configured before switching and is added to the capacitor corresponding to the capacitance Co of the occupant and the capacitor corresponding to the capacitance of the circuit through switching.

Accordingly, the total capacitance of the circuit becomes "Co+Cc+Cs" by switching and the amount Q1 of charge stored in the circuit before switching the switch is maintained, such that the voltage determined by three capacitances is determined as shown in Equation 2 below.

$$Vs = Q1 / (Co + Cc + Cs) \qquad \text{Equation 2}$$

As shown in Equation 2, when the capacitance of the circuit is changed by switching, the charge stored before switching are distributed and the detection capacitor has an initial voltage value corresponding to Vs by such charge distribution. The voltage determined by the three capacitances corresponds to the voltage of the output terminal T of the discharge response signal generator 22.

The detection capacitor is continuously charged by the power supply voltage Vp supplied during the predetermined time period while switching the switch SW after determining the initial voltage Vs by charge distribution, such that the voltage thereof increases up to the power supply voltage.

Figure 6:
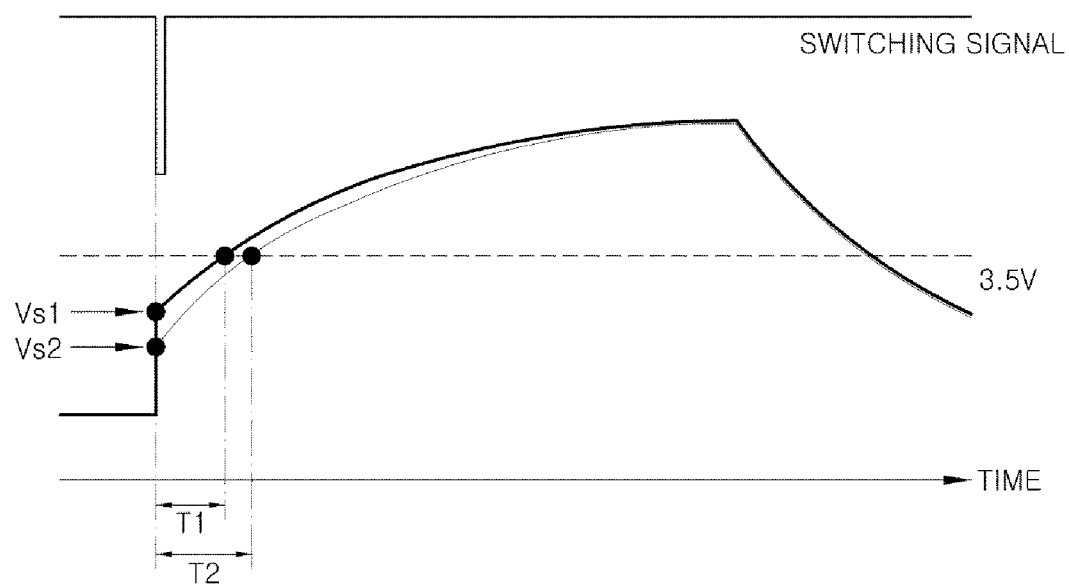
FIG. 6 is a diagram showing change in voltage of a detection capacitor according to operation of a switch in a discharge response signal generator applied to an occupant classification apparatus an exemplary embodiment according to an exemplary embodiment of the present invention.

Change in voltage of the detection capacitor Cs according to operation of the switch SW is shown in FIG. 6.

FIG. 6 is a diagram showing change in voltage of a detection capacitor according to operation of a switch in a discharge response signal generator applied to an occupant classification apparatus an exemplary embodiment according to an exemplary embodiment of the present invention.

As shown in FIG. 6, when a signal for controlling the switch SW is input by the controller 30, the initial voltages Vs1 and Vs2 of the detection capacitor Cs are determined by operation of the switch SW. As shown in Equation 2, the initial voltages Vs1 and Vs2 are determined by the amount of charge stored according to the capacitance of the occupant and the capacitance of the circuit before switching the switch SW. However, since the capacitance of the circuit is constant, the initial voltages Vs1 and Vs 2 are determined by the capacitance of the occupant. Accordingly, when the capacitance of the occupant is large, the initial voltages Vs1 and Vs2 may also be large. Of course, according to Equation 2, in the initial voltage (Vs of Equation 2), the capacitance Co of the occupant influences on a denominator, but is smaller than the capacitance of the circuit or the capacitance of the detection capacitor Cs and thus may be ignored.

Subsequently, the detection capacitor Cs is charged by the power supply voltage. When the detection capacitor is charged by the power supply voltage, the voltage of the detection capacitor Cs may exponentially increase according to a time constant determined by the voltage and capacitance of the circuit. When the switch SW is switched to connect the detection capacitor Cs to the line for connecting the power supply and the electrode device 10, since the resistance and capacitance of the circuit are substantially constant (influence of the capacitance of the occupant is low), a time required to increase the voltage of the detection capacitor Cs after the initial voltage Vs is substantially constant.

Accordingly, the voltage rising curve of the detection capacitor Cs is determined according to the levels of the initial voltages Vs1 and Vs2 determined by the amount of charge stored before switching the switch SW. As shown in FIG. 6, times T1 and T2 required to reach a specific voltage (e.g., 3.5 V; at this time, the power supply voltage Vp is 5V) may be changed according to the levels of the initial voltages Vs1 and Vs2.

As a result, the initial voltages Vs1 and Vs2 of the detection capacitor Cs after switching the switch SW are determined according to the amount of charge stored according to the capacitance Co of the occupant and the times T1 and T2 required for the voltage of the detection capacitor Cs to reach the specific voltage are changed according to the initial voltages Vs' and Vs2.

In several embodiments of the present invention, a difference in the times T1 and T2 required for the voltage of the detection capacitor Cs to reach the specific voltage is detected as a response to discharge of the charge stored according to the capacitance Co of the occupant according to switching of the switch SW, estimating the level of the capacitance Co of the occupant.

Referring to FIG. 1 again, the capacitance determination device 23 generates a signal for estimating the capacitance Co of the occupant using the voltage of the detection capacitor Cs output by the discharge response signal generator 22.

As described above, since the time required for the voltage of the detection capacitor Cs to reach the specific voltage is changed according to the initial voltage Vs of the detection capacitor Cs, the capacitance determination device 23 may generate a signal for estimating the capacitance Co of the occupant by detecting the time required for the voltage of the detection capacitor Cs output by the discharge response signal generator 22 to reach the specific voltage.

As shown in FIG. 1, in one exemplary embodiment of the present invention, the capacitance determination device 23 may include a reference signal generator 231 and a NAND logic element 232.

The reference signal generator 231 generates and outputs a reference signal under control of the controller 30. The NAND logic element 232 receives the voltage of the detection capacitor Cs output from the discharge response signal generator 22 and the reference signal output from the reference signal generator 231 and outputs a result of performing NAND logic operation with respect to the voltage of the detection capacitor Cs and the reference signal.

Figure 7:
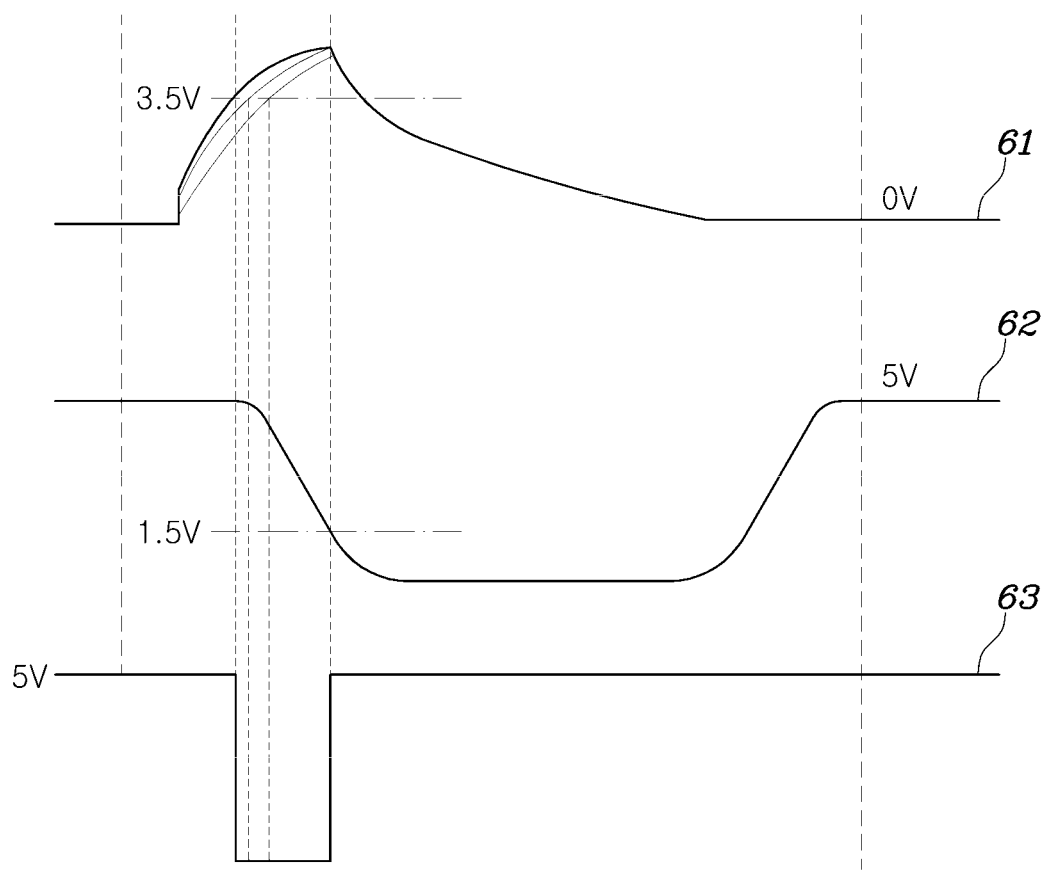
FIG. 7 is a diagram showing an example of change in voltage of a detection capacitor according to operation of a switch in a discharge response signal generator applied to an occupant classification apparatus an exemplary embodiment according to an exemplary embodiment of the present invention and a relationship between a reference signal output from a reference signal generator and a signal output from a NAND logic element.

FIG. 7 is a diagram showing an example of change in voltage of a detection capacitor according to operation of a switch in a discharge response signal generator applied to an occupant classification apparatus an exemplary embodiment according to an exemplary embodiment of the present invention and a relationship between a reference signal output from a reference signal generator and a signal output from a NAND logic element. In FIG. 7, reference numeral "61" denotes the output of the discharge response signal generator 22 shown in FIG. 6, that is, change in voltage of the detection capacitor Cs according to operation of the switch SW. Reference numeral 62 denotes an example of the reference signal output from the reference signal generator 231 and reference numeral 63 denotes the output of the NAND logic element 232.

As described with reference to FIG. 6, since the initial voltage of the detection capacitor Cs is changed by the difference in amount of charge stored according to the capacitance Co of the occupant, the time required for the output 61 of the discharge response signal generator 22 to increase up to the predetermined reference voltage (e.g., 3.5 V) in a process of storing charge until becoming the power supply voltage Vp is changed.

Although there are several methods of detecting such a time difference, in the example of FIG. 7, the time required for the output 61 of the discharge response signal generator 22 to increase up to the specific voltage (e.g., the power supply voltage Vp) after reaching the predetermined reference voltage (e.g., 3.5 V) is detected.

In the example of FIG. 7, the reference signal 62 generated by the reference signal generator 231 is shown as having a trapezoidal waveform having a predetermined gradient in rising and falling edges and may be changed according to hardware performance. In one exemplary embodiment of the present invention, the reference signal 62 has a logic high value in a period in which the voltage of the detection capacitor Cs increases from the initial voltage Vs and has a logic low value before decreasing to the predetermined reference voltage (e.g., 3.5 V) or less after the voltage of the detection capacitor Cs increases. For example, the reference signal 62 may be changed from the logic HIGH state to the logic LOW state in a period in which the switch SW of the discharge response signal generator 22 is switched to connect the detection capacitor Cs to the electrode device 10, to which the power supply voltage Vp is applied, and the voltage of the capacitor Cs increases from the initial voltage to the power supply voltage Vp.

The output 61 of the discharge response signal generator 22 input to the NAND logic element 232 operating between 0 and 5V is recognized as a logic low value in the NAND logic element 232 before becoming 3.5 V. As described above, since the time required for the output 61 of the discharge response signal generator 22 to increase up to the predetermined reference voltage (e.g., 3.5 V) in a process of storing charge until becoming the level of the power supply voltage Vp is changed by the difference in the initial voltage of the detection capacitor Cs generated according to the level of the capacitance Co of the occupant, a time when the output 61 of the discharge response signal generator 22 input to the NAND logic element 232 is recognized as having a logic HIGH value is changed.

Thereafter, when the reference signal decreases to 1.5 V, the signal input to the NAND logic element 232 is recognized as having a logic LOW value.

The NAND logic element 232 outputs the logic LOW value only when the two inputs are at a logic HIGH level. Accordingly, the time when the output 61 of the discharge response signal generator 22 is recognized as being at a logic HIGH level by the NAND logic element 232 is changed according to the capacitance Co of the occupant and the time when the reference signal 62 is recognized as being at the logic LOW level is fixed regardless of the capacitance Co of the occupant, such that the time when the output 63 of the NAND logic element 232 is maintained at the logic LOW level is changed according to the capacitance Co of the occupant.

As a result, in one exemplary embodiment of the present invention, it is possible to estimate the capacitance Co of the occupant according to the time when the output 63 of the NAND logic element 232 is maintained at the logic LOW level.

Referring to FIG. 1 again, the moisture detector 24 may detect change in electrical resistance according to moisture contained in the occupant to detect change in moisture when the occupant is seated in the electrode device 10. For example, when the occupant is located in the measurement area R1 by the electric field generated in the measurement area R1 by the electrode device 10, the electrical resistance of the occupant may be regarded as being connected between the electrode device 10 and the ground. The electrical resistance of the occupant may be significantly influenced by moisture contained in the occupant. An occupant containing a large amount of moisture forms smaller electrical resistance as compared to an occupant containing a small amount of moisture.

Accordingly, the moisture detector 24 may detect the amount of moisture contained in the occupant by detecting change in current according to change in electrical resistance in a state of applying a predetermined voltage to the electrode device 10.

The moisture detector 24 may be implemented by various moisture sensors or moisture detecting circuits widely known in this Field of the Invention.

The analog/digital converter (hereinafter, referred to as ADC) 25 may convert the signal output from the capacitance determination device 23 and the signal output from the moisture detector 24 into digital values recognized by the controller 30. That is, the analog/digital converter generates and delivers a digital value indicating the value (magnitude of the pulse) corresponding to the time when the logic LOW state of the signal output from the capacitance determination device 23 is maintained and a digital value indicating change in current detected by the moisture detector 24 to the controller 30.

The controller 30 may estimate the occupant using the signal delivered from the occupant property measurement device 20. For example, critical ranges associated with capacitance and the amount of moisture according to occupant type may be pre-set in a memory provided in the controller 30. That is, critical ranges according to occupant type based on the capacitance and the amount of moisture, which are information corresponding to the signal provided by the occupant property measurement device 20, may be set and stored in the controller 30 in advance, as shown in FIG. 8.

Figure 8:
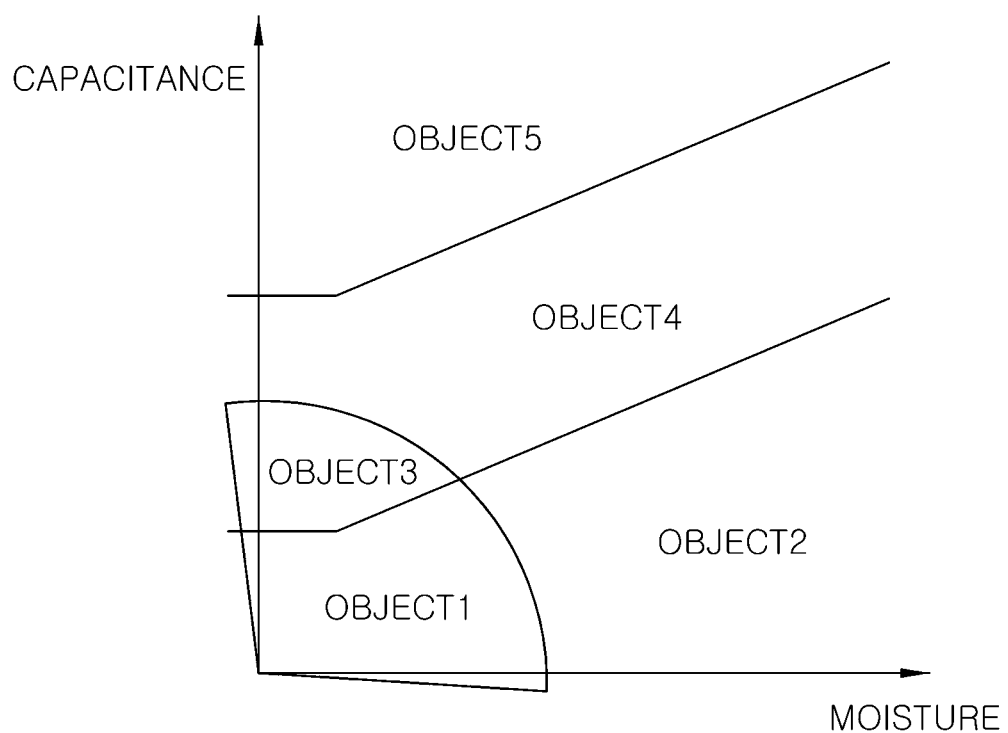
FIG. 8 is a graph showing a critical range for identifying the type of an occupant applied to a controller of an occupant classification apparatus an exemplary embodiment according to an exemplary embodiment of the present invention.

When the critical ranges are set according to occupant type as shown in FIG. 8, the controller 30 may estimate an occupant type as one of objects 01 to 05 using the signal delivered from the occupant property measurement device 20.

As described above, the occupant classification apparatuses according to several embodiments of the present invention may detect change in voltage generated by discharging charge stored according to capacitance of an occupant and change in current according to the amount of moisture contained in the occupant to estimate the occupant, without applying an algorithm requiring complex operation to classify occupants.

In particular, in the several embodiments of the present invention, since the occupant can be estimated by applying a low DC voltage, it is possible to omit several parts used for applying an AC voltage in a conventional occupant classification apparatus and, more particularly, expensive parts. Therefore, it is possible to reduce costs.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An occupant classification apparatus comprising:
an electrode device for detecting an occupant seated in a seat;
an occupant property measurement apparatus for measuring capacitance of and an amount of moisture contained in the occupant detected by the electrode device; and
a controller configured for estimating the occupant based on the capacitance and the amount of moisture measured by the occupant property measurement apparatus,
wherein the occupant property measurement apparatus includes:
a discharge response signal generator for generating a discharge response signal corresponding to an amount of charge stored according to the capacitance of the occupant detected by the electrode device;
a capacitance determination circuit for generating a signal configured for estimating the capacitance of the occupant from the discharge response signal; and
a moisture detector for detecting the amount of moisture contained in the occupant according to change in electrical resistance of the occupant detected by the electrode device, and
wherein the discharge response signal generator applies a direct current (DC) power supply voltage to the electrode device to store charge according to the capacitance of the occupant detected by the electrode device and discharges the charge stored according to the capacitance of the occupant to generate the discharge response signal corresponding to the amount of charge stored according to the capacitance of the occupant.

2. The occupant classification apparatus according to claim 1, wherein the electrode device includes first and second electrodes mounted to overlap each other and configured to receive the DC power supply voltage and to generate an electric field.

3. The occupant classification apparatus according to claim 2, wherein the first electrode is placed adjacent to a predetermined area, in which the occupant is seated, of the seat, the second electrode is placed at an opposite side thereof, and a first-electrode-direction electric field generated by the second electrode blocks a second-electrode-direction electric field generated by the first electrode.

4. The occupant classification apparatus according to claim 1, wherein the discharge response signal generator includes:
a power supply for providing the DC power supply voltage to the electrode device;
a detection capacitor; and
a switch for selectively determining an electrical connection between the electrode device and the power supply and an electrical connection between the electrode device and the detection capacitor, wherein, when the switch establishes the electrical connection between the electrode device and the detection capacitor, a power supply voltage is applied to the detection capacitor during a predetermined time period, and a voltage of the detection capacitor is the discharge response signal.

5. The occupant classification apparatus according to claim 4, wherein the controller is configured to control the switch to establish the electrical connection between the electrode device and the detection capacitor in a state of establishing the electrical connection between the electrode device and the power supply to perform charging by the capacitance of the occupant detected by the electrode device, wherein the charge stored according to the capacitance of the occupant detected by the electrode device is discharged, the discharged charge is provided to the detection capacitor to form an initial voltage of the detection capacitor, and the detection capacitor is charged by the power supply voltage provided during the predetermined time period after forming the initial voltage.

6. The occupant classification apparatus according to claim 5, wherein the capacitance determination circuit outputs the generated signal including change in the voltage of the detection capacitor increasing from the initial voltage as the generated signal configured for estimating the capacitance.

7. The occupant classification apparatus according to claim 6, wherein the capacitor determination circuit includes:
 a reference signal generator for generating a reference signal having a logic high value in a period in which the voltage of the detection capacitor increases from the initial voltage and having a logic low value before the voltage of the detection capacitor decreases to a predetermined reference voltage or less after increasing the voltage of the detection capacitor; and
 a NAND logic element for receiving the voltage of the detection capacitor and the reference signal and outputting a result of performing a NAND logic operation with respect to the voltage of the detection capacitor and the reference signal.

8. The occupant classification apparatus according to claim 1, wherein the moisture detector detects change in current according to change in electrical resistance of the occupant detected by the electrode device in a state of applying the DC power supply voltage to the electrode device to detect the amount of moisture contained in the occupant.

9. The occupant classification apparatus according to claim 1, wherein the controller includes predetermined ranges associated with the capacitance of the occupant and the amount of moisture contained in the occupant according to a type of the occupant and is configured to determine a predetermined range, to which the capacitance of the occupant and the amount of moisture measured by the occupant property measurement apparatus belong, to determine the type of the occupant seated in the seat.

10. An occupant classification apparatus comprising:
 an electrode device for receiving a direct current (DC) power supply voltage, wherein an electric field is formed in a measurement area, in which an occupant is located, to sense the occupant seated in a seat;
 an occupant property measurement apparatus for providing the DC power supply voltage to the electrode device, generating a first signal corresponding to a capacitance of the occupant based on another signal generated by discharging charge stored according to the capacitance of the occupant in the measurement area and generating a second signal corresponding to an amount of moisture contained in the occupant based on change in electrical resistance of the occupant detected in the measurement area; and
 a controller configured for estimating the occupant based on the first signal corresponding to the capacitance of the occupant and the second signal corresponding to the amount of moisture contained in the occupant,
 wherein the occupant property measurement apparatus:
  selectively and electrically connects the electrode device to the DC power supply voltage and a detection capacitor under control of the controller, and
  performs charging by the capacitance of the occupant detected in the measurement area, when an electrical connection between the electrode device and the DC power supply voltage is established, and discharges the charge stored according to the capacitance of the occupant detected in the measurement area, provides the discharged charge to the detection capacitor to form an initial voltage of the detection capacitor and charges the detection capacitor by the DC power supply voltage during a predetermined time period after forming the initial voltage of the detection capacitor, when an electrical connection between the electrode device and the detection capacitor is established.

11. The occupant classification apparatus according to claim 10, wherein the occupant property measurement apparatus outputs information based on a time required for a voltage of the detection capacitor to increase from the initial voltage of the detection capacitor to a predetermined reference voltage as the first signal corresponding to the capacitance of the occupant.

* * * * *